(12) United States Patent
Wang et al.

(10) Patent No.: US 12,423,817 B2
(45) Date of Patent: Sep. 23, 2025

(54) BRAIN NETWORK AND BRAIN ADDICTIVE CONNECTIVITY COMPUTING METHOD AND DEVICE

(71) Applicant: SHENZHEN INSTITUTES OF ADVANCED TECHNOLOGY CHINESE ACADEMY OF SCIENCES, Shenzhen (CN)

(72) Inventors: Shuqiang Wang, Shenzhen (CN); Changhong Jing, Shenzhen (CN)

(73) Assignee: SHENZHEN INSTITUTES OF ADVANCED TECHNOLOGY CHINESE ACADEMY OF SCIENCES, Shenzhen (CN)

( * ) Notice: Subject to any disclaimer, the term of this patent is extended or adjusted under 35 U.S.C. 154(b) by 400 days.

(21) Appl. No.: 18/090,490

(22) Filed: Dec. 29, 2022

(65) Prior Publication Data

US 2023/0196578 A1  Jun. 22, 2023

Related U.S. Application Data

(63) Continuation of application No. PCT/CN2022/076041, filed on Feb. 11, 2022.

(30) Foreign Application Priority Data

Dec. 16, 2021 (CN) .......................... 202111536650.4

(51) Int. Cl.
*G06T 7/00* (2017.01)
*A61B 5/00* (2006.01)
(52) U.S. Cl.
CPC .......... *G06T 7/0014* (2013.01); *A61B 5/4064* (2013.01); *G06T 2207/20081* (2013.01);
(Continued)

(58) Field of Classification Search
CPC ......... G06T 7/0014; G06T 2207/20081; G06T 2207/20084; G06T 2207/30016;
(Continued)

(56) References Cited

U.S. PATENT DOCUMENTS

| 2007/0112585 | A1* | 5/2007 | Breiter | ................... G16B 40/20 705/2 |
| 2011/0028827 | A1* | 2/2011 | Sitaram | ................ A61B 5/7267 600/410 |

(Continued)

FOREIGN PATENT DOCUMENTS

| CN | 108960341 A | 12/2018 |
| CN | 109376751 A | 2/2019 |

(Continued)

*Primary Examiner* — Van D Huynh

(57) ABSTRACT

A brain network and brain addictive connectivity computing method and device are disclosed. The method includes: obtaining real brain functional magnetic resonance (fMRI) images associated with different labels; generating first brain topologies associated with the different labels based on at least one training real brain fMRI image sample; generating a brain addiction standard feature map based on an additive real brain fMRI image; determining an initial weight value of each of the first brain topologies according to the brain addiction standard feature map; training an addictive brain network analysis model based on the first brain topologies associated with different labels and the initial weight value of each first brain topology; inputting at least one testing real brain fMRI image sample into addictive brain network analysis model to generate first weighted brain topologies.

16 Claims, 5 Drawing Sheets

(52) U.S. Cl.
CPC .............. *G06T 2207/20084* (2013.01); *G06T 2207/30016* (2013.01)

(58) Field of Classification Search
CPC ......... G06T 2207/10088; G06T 7/0012; A61B 5/4064; A61B 5/055; A61B 5/7267
See application file for complete search history.

(56) References Cited

U.S. PATENT DOCUMENTS

| | | | |
|---|---|---|---|
| 2014/0222738 A1* | 8/2014 | Joyce ..................... | G06N 3/10 706/47 |
| 2016/0066838 A1* | 3/2016 | DeCharms ........... | A61B 5/4064 434/236 |
| 2021/0106288 A1* | 4/2021 | Howard ................ | G16H 20/70 |
| 2022/0079515 A1* | 3/2022 | Woo ..................... | A61B 5/4824 |
| 2022/0122250 A1* | 4/2022 | Besson ................. | G06T 7/0012 |
| 2022/0293244 A1* | 9/2022 | Leuthardt .......... | G01R 33/4806 |
| 2023/0107263 A1* | 4/2023 | Kashiwagi ........... | A61B 5/7267 600/410 |

FOREIGN PATENT DOCUMENTS

| | | | |
|---|---|---|---|
| CN | 110298364 A | 10/2019 | |
| CN | 110428012 A | 11/2019 | |
| CN | 110522448 A | 12/2019 | |
| CN | 111067522 A | 4/2020 | |

* cited by examiner

BRAIN NETWORK AND BRAIN ADDICTIVE CONNECTIVITY COMPUTING METHOD AND DEVICE

CROSS-REFERENCE TO RELATED APPLICATIONS

This application is a United States national stage application of co-pending International Patent Application Number PCT/CN2022/076041, filed on Feb. 11, 2022, which claims the priority and benefit of Chinese patent application 202111536650.4, entitled "Brain Network and Brain Addictive connectivity Computing Method and Device" and filed on Dec. 16, 2021 with China National Intellectual Property Administration, the entire contents of which are incorporated herein by reference.

TECHNICAL FIELD

The present application relates to the technical field of artificial intelligence, and more particularly relates to a brain network and brain addictive connectivity computing method and device.

BACKGROUND

Significant progress has been made in information technology and medical imaging technology represented by artificial intelligence. The use of machine learning algorithms to analyze magnetic resonance images, carry out research on brain network computing methods, and promote the rapid development of artificial intelligence in the field of brain science is of great significance to the development of brain science and the exploration of the nicotine addiction mechanism in the brain.

Functional Magnetic Resonance Imaging (fMRI) technology achieves the purpose of non-invasive observation of changes in brain activity by detecting changes in cerebral blood oxygen saturation. Functional magnetic resonance imaging enables precise localization of specific brain active cortical regions and capture of changes in blood oxygen that reflect neuronal activity. With the continuous development of neuroimaging, functional MRI technology is increasingly applied to brain network analysis.

For the time being, for addictive brain network analysis, a brain fMRI image is usually reduced in dimension by compression or downsampling, and the dimension-reduced image is input into the model. Alternatively, a brain fMRI image may be sliced, and the slices in different directions would be input into the machine learning model, so as to identify and detect abnormal brain regions related to brain addiction.

The dimensionality reduction method will cause loss of fMRI image information. The slicing method relies on the prior knowledge and operations of professional physicians, and inputting the sliced images into the machine learning model will affect the performance of the machine learning model and cannot effectively analyze the structure of the addictive brain network.

SUMMARY

Embodiments of the present application provide a brain network and brain addictive connectivity computing method and device, which can effectively learn addiction-related abnormal brain topological features while retaining individual differences between different addictive brains, so as to accurately analyze the brain network of the addictive brain and improve the overall performance of the model.

According to a first aspect, embodiments of the present application provide a brain network and brain addictive connectivity computing method, including the following operations: capturing real brain functional magnetic resonance fMRI images associated with different labels, where the different labels are used to indicate different concentrations of an addictive substance, the real brain functional magnetic resonance fMRI images include a plurality of real brain regional fMRI images, and the real brain fMRI images associated with different labels include training real brain fMRI image samples and testing real brain fMRI image samples; generating first brain topologies associated with the different labels based on the training real brain fMRI image samples; obtaining addictive real brain fMRI images; generating a brain addiction standard feature map based on the addictive real brain fMRI images; determining the initial weight value of each first brain topology based on the brain addiction standard feature map; based on the first brain topologies associated with the different labels and the initial weight value of each first brain topology, training an addictive brain network analysis model; and inputting testing real brain fMRI image samples into the addictive brain network analysis model to generate first weighted brain topologies, where the first weighted brain topologies are respective weighted brain topology associated with the different labels.

In the above method, the first brain topology of different labels is generated based on the training real brain fMRI image samples, meaning to obtain the brain topological connectivity according to the existing brain medical images. Different from pure image information, brain topology can provide connectivity information between multiple brain regions, and the generated brain addiction standard feature map retains the neurobiological information between the addictive brain regions, and further the initial weight values between different brain regions in the first brain topology are determined. Then the addiction network analysis model is trained by the first brain topologies associated with different labels and the initial weight value of each first brain topology, which can effectively learn the connectivity information between different brain regions in the first brain topologies associated with different labels while retaining the individual differences between different addictive brains. Finally, according to the generated first weighted brain topologies, the abnormal brain topological features related to addiction are obtained, so as to accurately analyze the brain network of the addicted brain.

In a possible implementation, generating first brain topologies associated with the different labels based on the training real brain fMRI image samples may include: obtaining a brain atlas template; and generating first brain topologies associated with the different labels based on the training real brain fMRI image samples and the brain atlas template.

In the embodiments of the present application, obtaining the first brain topology does not need to be extracted through a limited template provided by the software; instead, by directly inputting the brain atlas template and the training real brain fMRI image samples, the first brain topologies associated with the different labels may be generated. The whole process is very simple, which improves the flexibility of using brain atlas templates and the efficiency of obtaining brain topological connectivity from brain medical images.

In a possible implementation, inputting testing real brain fMRI image samples into the addictive brain network analysis model to generate a first weighted brain include: generating the second brain topologies associated with the different labels based on the testing real brain fMRI image samples; determining an initial weight value of each second brain topology according to the addictive brain network analysis model; and generating first weighted brain topologies based on the second brain topologies associated with the different labels and an initial weight value of each second brain topology.

In the embodiments of the present application, after the addictive brain network analysis model is trained, it is used for the test of the testing real brain fMRI image samples. During the test, the second brain topology is generated according to the testing real brain fMRI image samples, and then the weight values of the brain topology of the trained addiction brain network analysis model are used as the initial weight values of the second brain topology during the test. Then according to the second brain topologies and the initial weight value of each second brain topology, the first weighted brain topologies are generated to obtain the abnormal brain topological features related to addiction, so as to accurately analyze the brain network of the addicted brain.

In a possible implementation, the second brain topologies associated with the different labels include a second brain topology associated with the first label and a second brain topology associated with the second label. The first weighted brain topologies include a first weighted brain topology associated with the first label and a first weighted brain topology associated with the second label. The generating the first weighted brain topologies based on the second brain topologies associated with the different labels and the initial weight value of each second brain topology includes: inputting the second brain topology associated with the first label and the second brain topology associated with the second label into the addictive brain network analysis model; when the first label is the target label, generating the first weighted brain topology associated with the first label; and when the second label is the target label, generating the first weighted brain topology associated with the second label.

In the embodiments of the present application, the addictive brain network analysis model can generate the first weighted brain topologies associated with the different labels according to the different target labels. Multiple sets of real brain fMRI images associated with different labels may be trained and tested simultaneously, thereby improving the overall performance of the model.

In a possible implementation, training the addictive brain network analysis model based on the first brain topologies associated with the different labels and the initial weight value of each first brain topology includes: inputting the first brain topologies associated with different labels and the initial weight value of each first brain topology into the addictive brain network analysis model to be trained to generate second weighted brain topologies; determining a recognition result of each second weighted brain topology; training the addictive brain network analysis model based on the recognition result of each second weighted brain topology.

In the embodiments of the present application, the addictive brain network analysis model is trained according to the recognition result of each generated second weighted brain topology, so that the model can learn continuously until the second weighted brain topology that can deceive the model is generated, and so the learning ability of the model is improved.

In a possible implementation, training the addictive brain network analysis model according to the recognition result of each second weighted brain topology includes: obtaining the loss function of the addictive brain network analysis model according to the recognition result of each second weighted brain topology; and iteratively training the addictive brain network analysis model according to the loss function of the addictive brain network analysis model.

In the embodiments of the present application, the addictive brain network analysis model obtains the loss function of the model according to the recognition result of the second weighted brain topology. The loss function is used to iteratively train the addictive brain network analysis model, which can make the model better learn different sample features, so that the second weighted brain topologies learned by the model are closer to the topological characteristics of the real addictive brain network.

According to a second aspect, embodiments of the present application further provide a brain network and brain addictive connectivity computing device, including: an acquisition unit configured to capture real brain functional magnetic resonance fMRI images associated with different labels, where the different labels are used to indicate different concentrations of an addictive substance, the real brain functional magnetic resonance fMRI images include a plurality of real brain regional fMRI images, and the real brain fMRI images associated with different labels include training real brain fMRI image samples and testing real brain fMRI image samples; a processing unit used to generate first brain topologies associated with the different labels based on the training real brain fMRI image samples. The acquisition unit is used to obtain an addictive real brain fMRI image. The processing unit is configured to: generate a brain addiction standard feature map based on the addictive real brain fMRI image; determine an initial weight value of each first brain topology based on the brain addiction standard feature map; train an addictive brain network analysis model based on the first brain topologies associated with the different labels and the initial weight value of each first brain topology; and input the testing real brain fMRI image samples into the addictive brain network analysis model to generate first weighted brain topologies, where the first weighted brain topologies are respective weighted brain topologies associated with the different labels.

In a possible implementation, the acquisition unit is further configured to: obtain a brain atlas template. The processing unit is specifically configured to generate the first brain topologies associated with the different labels based on the training real brain fMRI image samples and the brain atlas template.

In a possible implementation, the processing unit is specifically configured to: generate the second brain topologies associated with the different labels based on the testing real brain fMRI image samples; determine an initial weight value of each second brain topology according to the addictive brain network analysis model; and generate first weighted brain topologies based on the second brain topologies associated with the different labels and an initial weight value of each second brain topology.

In a possible implementation, the processing unit is specifically configured for: inputting the second brain topology associated with the first label and the second brain topology associated with the second label into the addictive brain network analysis model; when the first label is the target label, generating the first weighted brain topology associated with the first label; and when the second label is the target label, generating the first weighted brain topology associated with the second label.

In a possible implementation, the processing unit is specifically configured for: inputting the first brain topologies associated with different labels and the initial weight value of each first brain topology into the addictive brain network analysis model to be trained to generate second weighted brain topologies; determining a recognition result of each second weighted brain topology; and training the addictive brain network analysis model according to the recognition result of each second weighted brain topology.

In a possible implementation, the acquisition unit is further configured to: obtaining the loss function of the addictive brain network analysis model according to the recognition result of each second weighted brain topology. The processing unit is specifically configured to iteratively train the addictive brain network analysis model based on the loss function of the addictive brain network analysis model.

For operations performed by and beneficial effects of the addictive brain network analysis device, reference may be made to the method and beneficial effects described in any one of the above-mentioned first aspects, and the same description will not be repeated.

According to a third aspect, the present application provides a brain network and a brain addictive connectivity computing device, where the addictive brain network analysis device may be a server, a device in a server, or a device that may be matched with the server. The addictive brain network analysis device can also be a chip system. The addictive brain network analysis device can perform the method described in any one of the first aspect. The function of the addictive brain network analysis device may be realized by hardware, and can also be realized by executing corresponding software by hardware. The hardware or software includes one or more modules corresponding to the above functions. The module may be software and/or hardware. For operations performed by and beneficial effects of the addictive brain network analysis device, reference may be made to the method and beneficial effects described in any one of the above-mentioned first aspects, and the same description will not be repeated.

According to a fourth aspect, the present application provides a brain network and a brain addictive connectivity computing device. The addictive brain network analysis device includes a processor, and when the processor invokes a computer program in a memory, the method according to any one of the first aspects is performed.

According to a fifth aspect, the present application provides a brain network and a brain addictive connectivity computing device. The addictive brain network analysis device includes a processor and a memory. The memory is used to store a computer program. The processor is configured to execute the computer program stored in the memory, so that the addictive brain network analysis device executes the method according to any one of the first aspects.

According to a sixth aspect, the present application provides a brain network and a brain addictive connectivity computing device. The addictive brain network analysis device includes a processor, a memory and a transceiver. The transceiver is used for receiving channels or signals, or transmitting channels or signals. The memory is used to store computer programs. The processor is configured to invoke the computer program from the memory to perform the method according to any one of the first aspects.

According to a seventh aspect, the application provides a brain network and a brain addictive connectivity computing device, which includes a processor and an interface circuit. The interface circuit is used to receive a computer program and transmit it to the processor. The processor runs the computer program to perform the method of any one of the first aspects.

According to an eighth aspect, the present application provides a computer-readable storage medium for storing a computer program. The computer program, when executed, causes the method according to any one of the first aspects to be performed.

According to a ninth aspect, the present application provides a computer program product comprising a computer program. The computer program, when executed, causes a method as described in any one of the first aspects to be implemented.

According to a tenth aspect, embodiments of the present application provide an addictive brain network analysis system, which includes at least one server and at least one terminal device. The server is configured to perform the steps of any one of the above-mentioned first aspect.

BRIEF DESCRIPTION OF DRAWINGS

The accompanying drawings used in the embodiments of the present application will be introduced below.

DETAILED DESCRIPTION OF EMBODIMENTS

Figure 1:
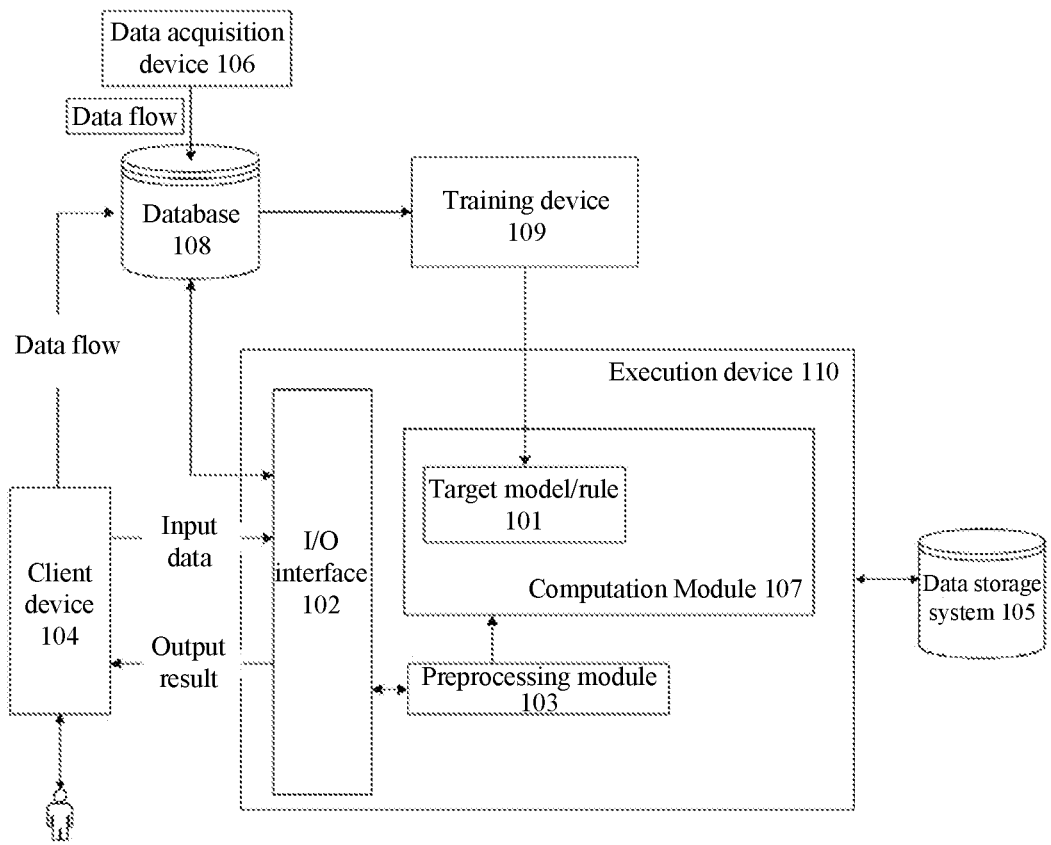
FIG. 1 is a schematic diagram of an architecture of an addictive brain network analysis system provided by an embodiment of the present application.

Embodiments of the present application will be described below with reference to the accompanying drawings in the embodiments of the present application.

Since the embodiments of the present application involve a large number of applications of neural networks, for ease of understanding, related terms and related concepts such as neural networks involved in the embodiments of the present application are first introduced below.

(1) Neural Network

A neural network may be composed of neural units. A neural unit may refer to an operation unit that takes $X_s$ and intercept 1 as inputs, and the output of the operation unit may be:

$$h_{W,b}(x) = f(W^T x) = f(\Sigma_{s=1}^{n} W_s x_s + b) \qquad (1\text{-}1)$$

where s=1, n; n is a natural number greater than 1, $W_s$ is a weight of $X_s$, and b is a bias of the neural unit; f is an activation function of the neural unit and is used to introduce nonlinear characteristics into the neural network to convert an input signal to the neural unit into an output signal. The output signal of this activation function may be used as the input of a next convolutional layer. The activation function may be a sigmoid function. A neural network is a network formed by connecting many of the above single neural units together. That is, the output of one neural unit may be the input of another neural unit. The input of each neural unit may be connected with a local receptive field of a previous layer to extract the features of the local receptive field. The local receptive field may be a region composed of several neural units.

(2) Deep Neural Network

Deep neural network (DNN), also known as multi-layer neural network, may be understood as a neural network with many hidden layers; of course, there is no a specific metric for "many" here. For purposes of division of DNN depending on the positions of different layers, the neural network inside DNN may be divided into three categories: input layer, hidden layer, and output layer. Generally speaking, the first layer is the input layer, the last layer is the output layer, and the intermediate layers are all hidden layers. These layers are fully connected, that is, each and every neuron in an i-th layer must be connected to each and every neuron in the (i+1)-th layer. Although it looks complicated, DNN is not complicated in terms of the work of each layer. Simply put, it may be expressed as the following linear relationship: $y=\alpha(Wx+b)$, where x is an input vector, y is an output vector, b is an offset vector, W is a weight matrix (also known as coefficients), and $\alpha(\ )$ is an activation function. Each layer just performs such a simple operation on the input vector x to get the output vector y. Due to the large number of DNN layers, the numbers of coefficients W and offset vectors b are also large. These parameters are defined in DNN as follows. Take coefficients W as an example. Suppose in a three-layer DNN, the linear coefficient from the fourth neuron in the second layer to the second neuron in the third layer is defined as $W_{24}^3$, where the superscript 3 represents the number of the layer where the coefficient W is located, and the subscripts correspond to the output third layer index 2 and the input second layer index 4. In a word, the coefficient from the kth neuron in the L−1 layer to the j-th neuron in the Lth layer is defined as $W_{jk}^L$. It should be noted that the input layer does not have the W parameter. In a deep neural network, more hidden layers make the network more capable of depicting complex situations in the real world. In theory, the model with more parameters is more complex, and the "capacity" is larger, which means that it can complete more complex learning tasks. Training the deep neural network is the process of learning the weight matrix, and its ultimate goal is to obtain the weight matrix of all layers of the trained deep neural network (the weight matrix formed by the vectors W of many layers).

(3) Convolutional Neural Network

A convolutional Neural Network (CNN) is a deep neural network with a convolutional structure. A convolutional neural network includes a feature extractor consisting of a convolutional layer and a subsampling layer. The feature extractor may be viewed as a filter, and the convolution process may be viewed as convolution with an input image or a convolutional feature map using a trainable filter. The convolutional layer refers to the neuron layer in the convolutional neural network that performs convolution processing on the input signal. In a convolutional layer of a convolutional neural network, a neuron may be connected only to some of its neighbors. A convolutional layer usually contains several feature planes, and each feature plane may be composed of some neural units arranged in a rectangle. Neural units in the same feature plane share weights, and the shared weights here are a convolution kernel. Shared weights may be understood as that the way to extract image information is independent of location. The underlying principle is that one portion of the image has the same statistics as other portions. This means that image information learned in one portion can also be used in another portion. So for all positions on the image, the same learned image information may be used. In the same convolutional layer, multiple convolution kernels may be used to extract different image information. Generally, the more the number of convolution kernels, the richer the image information reflected by the convolution operation.

The convolution kernel may be initialized in the form of a matrix of a random size, and the convolution kernel can obtain reasonable weights by learning during the training process of the convolutional neural network. In addition, the immediate benefit of sharing weights is to reduce the connections between the layers of the convolutional neural network, while reducing the risk of overfitting.

(4) Recurrent Neural Networks (RNN) are used to process sequence data. In the traditional neural network model, from the input layer to the hidden layer to the output layer, the layers are fully connected, while for the various nodes in each layer, there is no connection between them. Although this ordinary neural network has solved many problems, it is still powerless to many problems. For example, if you want to predict the next word of a sentence, you generally need to use the previous words, because the words earlier and later in a sentence are not independent of each other. The reason why RNN is called a recurrent neural network is that the current output of a sequence is also related to the previous output. In particular, the network will memorize the previous information and apply it to the calculation of the current output, that is, the nodes in the hidden layers are no longer unconnected but connected, and the input of the hidden layer not only includes the output of the input layer but also includes the output of the hidden layer at the previous moment. In theory, RNN can process sequence data of any length. The training of RNN is identical with the training of traditional CNN or DNN. The error backpropagation algorithm is also used, but there is one difference: if the RNN is expanded into a network, its parameters, such as W, are shared; however, this is not the case with the traditional neural network as exemplified above. Furthermore, in the gradient descent algorithm, the output of each step depends not only on the network of the current step, but also on the state of the network in the previous steps. This learning algorithm is called Back Propagation Through Time (BPTT).

Why use a recurrent neural network when you already have a convolutional neural network? The reason is very simple. In the convolutional neural network, there is a premise that the elements are independent of each other, and the input and output are also independent, such as cats and dogs. But in the real world, many elements are interconnected, for example, the change of stocks over time. Another example is a person who says: "I like to travel, and my favorite place is Yunnan. I must go to _____ in the future". To fill in the blank here. Humans should know that it should be filled with "Yunnan". Because humans make inferences based on the content of the context, but how do you get machines to do this? RNN came into being. RNNs are designed to give machines the ability to memorize like humans do. Therefore, the output of RNN needs to rely on the current input information and historical memory information.

(5) Loss Function

In the process of training a deep neural network, because it is hoped that the output of the deep neural network is as close as possible to the value really wanted to be predicted, the predicted value of the current network may be compared with the target value that's really wanted, and then based on the difference between the two, the weight vector of each layer of neural network may be updated (of course, there is usually an initialization process before the first update, that is, to pre-configure parameters for each layer in the deep neural network). For example, if the predicted value of the network is high, the weight vector may be adjusted to make the prediction lower, and keep adjusting until the deep neural network can predict the real desired target value or a value that is very close to the real desired target value. Therefore, it is needed to pre-define "how to compare the difference between the predicted value and the target value", which is the loss function or objective function. They are important equations for measuring the difference between predicted and target values. Taking the loss function as an example, the higher the output value of the loss function (loss), the greater the difference, then the training of the deep neural network becomes the process of reducing the loss as much as possible.

(6) Back Propagation Algorithm

The convolutional neural network can use the error back propagation (BP) algorithm to correct the sizes of the parameters in the initial super-resolution model during the training process, so that the reconstruction error loss of the super-resolution model becomes smaller and smaller. Specifically, passing the input signal forward until to the output will generate error loss, and the parameters in the initial super-resolution model are updated by back-propagating the error loss information, so as to make the error loss converge. The back-propagation algorithm is a back-propagation motion dominated by the error loss, aiming to obtain the parameters of the optimal super-resolution model, such as the weight matrix.

(7) Generative Adversarial Networks

A generative Adversarial Network (GAN) is a deep learning model. The model includes at least two modules: one is the Generative Model, the other is the Discriminative Model, and the two modules learn from each other through game play to produce better output. Both the generative model and the discriminative model may be neural networks, specifically deep neural networks or convolutional neural networks. The basic principle of GAN is as follows. Take the GAN that generates pictures as an example, suppose there are two networks, G (Generator) and D (Discriminator), where G is a network that generates pictures, it receives a random noise z and generates a picture through this noise, denoted as G(z); D is a discriminative network, which is used to determine whether a picture is "real". Its input parameter is x, x represents a picture, and the output D(x) represents the probability that x is a real picture. If it is 1, it means that it is 100% a real picture. If it is 0, it means that it cannot be a real picture. In the process of training the generative adversarial network, the goal of the generative network G is to generate a real picture as much as possible to deceive the discriminant network D, and the goal of the discriminative network D is to try to distinguish the picture generated by G from a real picture as much as possible. In this way, G and D constitute a dynamic "game" process, that is, the "Adversarial" in the "generative adversarial network". As a final result of the game, in an ideal state, G can generate a picture G (2) that is very "real", while it is difficult for D to determine whether the picture generated by G is real, that is, D(G(z))=0.5. This results in an excellent generative model G, which may be used to generate pictures.

Referring to FIG. 1. FIG. 1 is a schematic diagram of an architecture of an addictive brain network analysis system provided by an embodiment of the present application. As shown in the FIG., the data acquisition device 106 is used to capture real brain fMRI images of different labels. In the embodiments of the present application, the data includes: real brain fMRI images of different labels; and the real brain fMRI images of different labels are stored in the database 108. The training device 109 trains a target model/rule 101 based on the real brain fMRI images of different labels in the database 108, wherein the target model/rule 101 may be an addictive brain network analysis model. Hereinafter, how the training device 109 derives the target model/rule 101 based on the training data set will be described in more detail. The target model/rule 101 may be used to implement the addictive brain network analysis method provided by the embodiments of the present application. That is, the real brain fMRI images associated with different labels are input into the target model/rule 101 after relevant preprocessing, and then the addictive brain network analysis model may be obtained. The target model/rule 101 in the embodiments of the present application may specifically be a generative adversarial network. In the embodiments provided in this application, the generative adversarial network may be obtained by training the model that needs to be trained. It should be noted that, in practical applications, the data in the database 108 does not necessarily come from the capturing of the data collection device 106, and may also be received from other devices. In addition, it should be noted that the training device 109 does not necessarily train the target model/rule 101 based on the training data set of the database 108, and it is also possible to obtain the training data set from the clouds or other places for model training. The above description should not be taken as a limitation on the embodiments of the present application.

The target model/rule 101 trained based on the training device 109 may be applied to different systems or devices, such as the execution device 110 shown in FIG. 1. The execution device 110 may be a terminal, such as a mobile phone terminal, a tablet computer, a notebook computer, an augmented reality/virtual reality (AR/VR), a vehicle-mounted terminal, etc., or a server or a cloud. In FIG. 1, the execution device 110 is configured with an I/O interface 102 for data interaction with an external device, and a user can input data to the I/O interface 102 through the client device 104.

The preprocessing module 103 is used for preprocessing the addictive real brain fMRI images received by the I/O interface 102. In the embodiments of the present application, the preprocessing module 103 may be used to generate a brain addiction standard feature map according to the addictive real brain fMRI images, so as to constrain the target model/rule 101.

When the execution device 110 preprocesses the addictive real brain fMRI images, or the calculation module 107 of the execution device 110 performs calculations and other related processings, the execution device 110 can call the data, codes, etc. in the data storage system 105 for corresponding processing, and can also store the data, instructions, etc. obtained by the corresponding processing in the data storage system 105.

Finally, the I/O interface 102 returns the processing results to the client device 104 for provision to the user.

It is worth noting that the training device 109 can generate corresponding target models/rule 101 based on different training data for different goals or tasks, and the corresponding target models/rule 101 may be used to achieve the above goals or complete the above tasks, thus providing the user with the desired result.

In the case shown in FIG. 1, the user can manually provide input data, which may be operated through the interface provided by the I/O interface 102. Alternatively, the client device 104 may automatically send input data to I/O interface 102. If the user's authorization is required to allow the client device 104 to automatically send the input data, the user can set corresponding permissions in the client device 104. The user can view the result output by the execution device 110 on the client device 104, and the specific presentation form may be a specific manner such as display, sound, or action. The client device 104 can also be used as a data acquisition terminal to collect the input data of the input I/O interface 102 and collect the output result of the output I/O interface 102 as shown in the FIG. as new sample data, and store them in the database 108. Of course, it is also possible not to collect through the client device 104, but the I/O interface 102 directly uses the input data input into the I/O interface 102 and the output result output from the I/O interface 102 as shown in the FIG. as new samples to be stored in database 108.

It is worth noting that FIG. 1 is only a schematic diagram of a system architecture provided by an embodiment of the present application, and the positional relationships between the features, devices, modules, etc. shown in the FIG. will not constitute any limitation. For example, in FIG. 1, data storage system 105 is an external memory relative to execution device 110. In other cases, the data storage system 105 may also be located in the execution device 110.

As shown in FIG. 1, the target model/rule 101 is obtained by training on the training device 109. The target model/rule 101 may be a generative adversarial network in the embodiments of the present application. Specifically, the generative adversarial network provided by the embodiments of the present application may include: a generative network and a discriminative network. In the generative adversarial networks provided by the embodiments of the present application, both the generative network and the discriminative network may be convolutional neural networks.

As mentioned in the introduction to the basic concepts above, a convolutional neural network is a deep neural network with a convolutional structure, and is a deep learning architecture. Deep learning architecture refers to multiple levels of learning at different levels of abstraction through machine learning algorithms. As a deep learning architecture, CNN is a feed-forward artificial neural network in which the various neurons can respond to an image input thereto.

Figure 2:
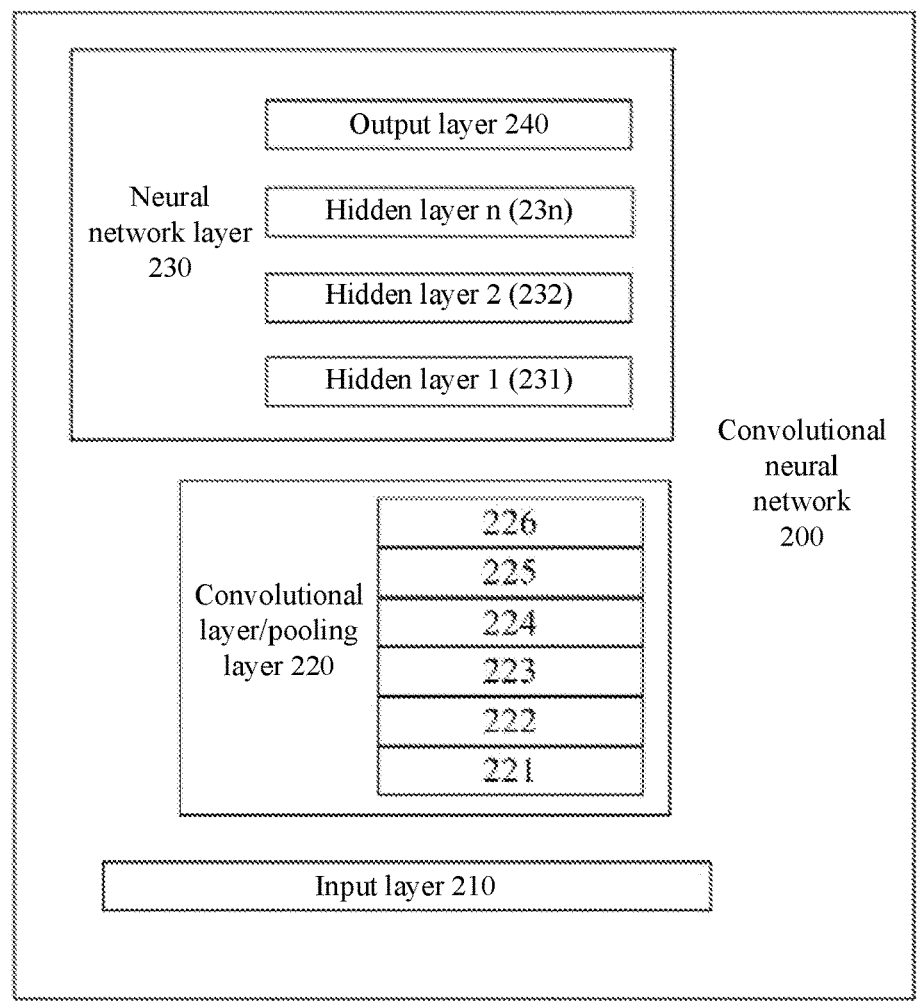
FIG. 2 is a schematic diagram of a convolutional neural network 200 provided by an embodiment of the present application.

Referring to FIG. 2, which is a schematic diagram of a convolutional neural network 200 provided by an embodiment of the present application. The convolutional neural network 200 may include an input layer 210, a convolutional layer/pooling layer 220, and a neural network layer 230. The above-mentioned convolutional layer/pooling layer 220 may include layers 221-226. For example, in one implementation, layer 221 is a convolutional layer, layer 222 is a pooling layer, layer 223 is a convolutional layer, layer 224 is a pooling layer, 225 is a convolutional layer, and 226 is a pooling layer. In another implementation, 221 and 222 are convolutional layers, 223 is a pooling layer, 224 and 225 are convolutional layers, and 226 is a pooling layer. That is, the output of the convolutional layer may be used as the input of the subsequent pooling layer, or it may be used as the input of another convolutional layer to continue the convolution operation.

The following will take the convolutional layer 221 as an example to introduce the inner working principle of a convolutional layer.

The convolutional layer 221 may include many convolution operators. The convolution operator, also known as a kernel, acts in model training as a filter that extracts specific information from the input image matrix. The convolution operator may be essentially a weight matrix. This weight matrix is usually predefined. In the process of convolving an image, the weight matrix usually performs the processing one eigenvalue by one eigenvalue or two eigenvalues by two eigenvalues along the horizontal direction on the input image vector, so as to complete the work of extracting specific features from the image. The size of this weight matrix should be related to the size of the image. It should be noted that the depth dimension of the weight matrix is the same as the depth dimension of the input image. During the convolution operation, the weight matrix is extended to the full depth of the input image. Therefore, convolving with a single weight matrix produces a convolutional output with a single depth dimension. But in most cases, instead of using a single weight matrix, multiple weight matrices of the same size (row x column) are applied, that is, multiple isotype matrices. The output of each weight matrix is stacked to form the depth dimension of the convolutional image, where the dimension may be understood as determined by the "multiple" mentioned above. The multiple weight matrices have the same size (row x column), and the sizes of the feature maps extracted from the multiple weight matrices with the same size are also the same, and then the multiple extracted features with the same size are combined to form the output of the convolution operation.

The weight values in these weight matrices need to be obtained after a lot of training in practical applications. The weight matrices formed by the weight values obtained by training may be used to extract information from the input image, thereby enabling the convolutional neural network 200 to make correct predictions.

When the convolutional neural network 200 has multiple convolutional layers, the initial convolutional layer (such as 221) often extracts more general features, which can also be called low-level features. As the depth of the convolutional neural network 200 deepens, the features extracted by the later convolutional layers (such as 226) become more and more complex, such as features with high-level semantics. The higher the semantics of the features, the more suitable they are for the problem to be solved.

Since the number of training parameters often needs to be reduced, it is often necessary to periodically introduce a pooling layer after the convolutional layer(s). In the layers 221-226 included in 220 in FIG. 2, it may be a convolutional layer followed by a pooling layer, or a multiple convolutional layers followed by one or more pooling layers.

After being processed by the convolutional layer/pooling layer 220, it is not yet sufficient for the convolutional neural network 200 to output the required output information. Because as mentioned before, the convolutional/pooling layer 220 will only extract features. However, in order to generate the final output information (the desired class information or other relevant information), the convolutional neural network 200 needs to utilize the neural network layer 230 to generate one or a set of outputs of the desired number of classes. Therefore, the neural network layer 230 may include multiple hidden layers (231, 232 to 23$n$ as shown in FIG. 2) and the output layer 240. The parameters contained in the multiple hidden layers may be obtained by pre-training based on the relevant training data of the specific task type. For example, the task types may include image recognition, image classification, image super-resolution reconstruction, and so on.

After the multiple hidden layers in the neural network layer 230, that is, the final layer of the entire convolutional neural network 200 is the output layer 240. The output layer 240 has a loss function similar to categorical crossentropy, and is specifically used to calculate the prediction error. Once the forward propagation of the entire convolutional neural network 200 (as shown in FIG. 2, the propagation from the direction 210 to 240 is forward propagation) is completed, the back propagation (as shown in FIG. 2, the propagation from the 240 to 210 direction is the back propagation) will be started to update the weight values and biases of the layers mentioned above, so as to reduce the loss of the convolutional neural network 200, and the error between the result outputted by the convolutional neural network 200 through the output layer and the ideal result.

It should be noted that the convolutional neural network 200 shown in FIG. 2 is only used as an example of a convolutional neural network. In specific applications, convolutional neural networks can also exist in the form of other network models.

Figure 3:
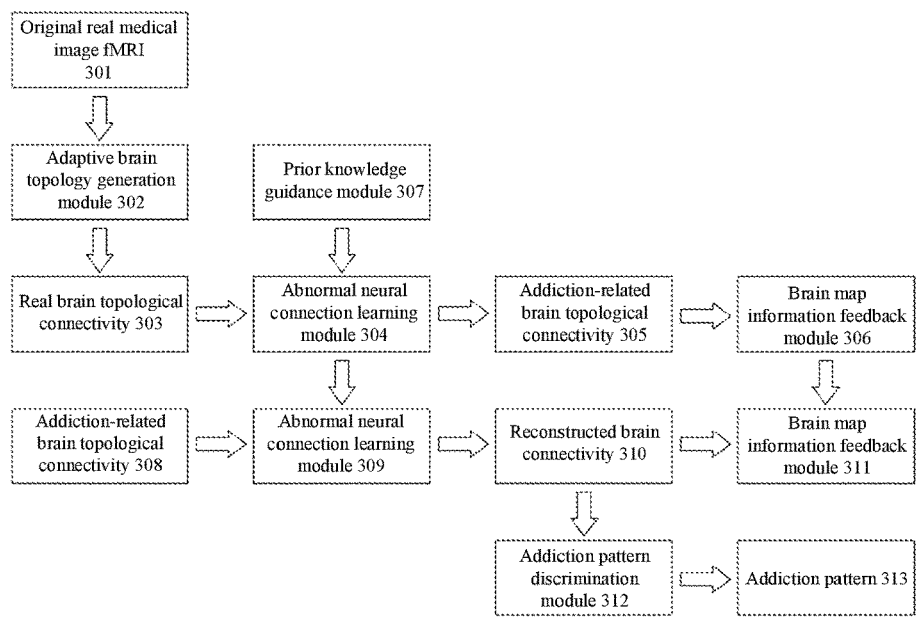
FIG. 3 is a schematic diagram of an addictive brain network analysis model provided by an embodiment of the present application.

Referring now to FIG. 3, which is a schematic diagram of an addictive brain network analysis model provided by an embodiment of the present application. The addictive brain network analysis model may include original real medical images fMRI 301, adaptive brain topology generation module 302, real brain topological connectivity 303, abnormal neural connection learning module 304, addiction-related brain topological connectivity 305, brain atlas information feedback module 306, prior knowledge guidance module 307, addiction-related brain topological connectivity 308, abnormal neural connection learning module 309, reconstructed brain connectivity 310, brain map information feedback module 311, addiction pattern discrimination module 312, and addiction pattern 313.

Original real medical images fMRI 301 include real brain fMRI images at different concentrations of an addictive substance. In the training of the addictive brain network analysis model, the real brain fMRI images at two different concentrations of an addictive substance are generally selected. For example, a high-concentration real brain fMRI image and a saline real brain fMRI image are used.

The original real medical images fMRI 301 are input into the adaptive brain topology generation module 302, and the real brain topological connectivity 303 is generated. The above-mentioned adaptive brain topology generation module 302 is used for generating real brain topological connectivity 303 from the original real medical image fMRI 301 adaptively according to the region of interest (ROI) divided by the brain atlas template. The above-mentioned real brain topological connectivity 303 generally includes two concentrations of real brain topological connectivity, for example, a high-concentration real brain topological connectivity and a normal saline real brain topological connectivity.

The real brain topological connectivity 303 is input into the abnormal neural connection learning module 304 to generate an addiction-related brain topological connectivity 305. The above-mentioned abnormal neural connection learning module 304 is used to learn the topological features of the brain network in the form of a graph structure in the non-Euclidean space, so as to effectively learn the connectivity information between different brain regions while retaining the individual differences between different patients. The above-mentioned addiction-related brain topological connectivity 305 may generally include addiction-related brain topological connectivity at one of two concentrations, for example, a high concentration addiction-related brain topological connectivity or a saline addiction-related brain topological connectivity.

The prior knowledge guidance module 307 is used to calculate the abnormal brain connection having been addictive, and determine the initial weight value of the real brain topological connectivity 303, so as to constrain the abnormal neural connection learning module 304 and the brain map information feedback module 306.

The addiction-related brain topological connectivity 305 is input into the brain atlas information feedback module 306, and the authenticity of the addiction-related brain topological connectivity 305 is judged, thereby constraining the abnormal neural connection learning module 304.

Addiction-related brain topological connectivity 308 can generally include the addiction-related brain topological connectivity at the other of two concentrations. For example, if addiction-related brain topological connectivity 305 is a high concentration addiction-related brain topological connectivity, then addiction-related brain topological connectivity 308 is saline addiction-related brain topological connectivity. If addiction-related brain topological connectivity 305 is saline addiction-related brain topological connectivity, then addiction-related brain topological connectivity 308 is high-concentration addiction-related brain topological connectivity.

The abnormal neural connection learning module 309 is trained by the abnormal neural connection learning module 304. Addiction-related brain topological connectivity 308 is input into abnormal neural connection learning module 309, and accordingly reconstructed brain connectivity 310 is generated. The above-mentioned reconstructed brain connectivity 310 is an addictive brain topological structure with the same size as the real brain topological connectivity 303, and generally includes an addictive brain topological structure at one of two concentrations.

The brain atlas information feedback module 311 is trained from the brain atlas information feedback module 306. The reconstructed brain connectivity 310 is input into the brain atlas information feedback module 311, and the authenticity of the reconstructed brain connectivity 310 is judged, thereby constraining the abnormal neural connection learning module 309.

The reconstructed brain connectivity 310 is input to the addiction pattern discrimination module 312, and the authenticity of the reconstructed brain connectivity 310 is discriminated, thereby constraining the abnormal neural connection learning module 309.

The addiction pattern 313 is the finally output addiction-related abnormal brain topological features, which may be used to accurately analyze the brain network of the addicted brain.

Figure 4:
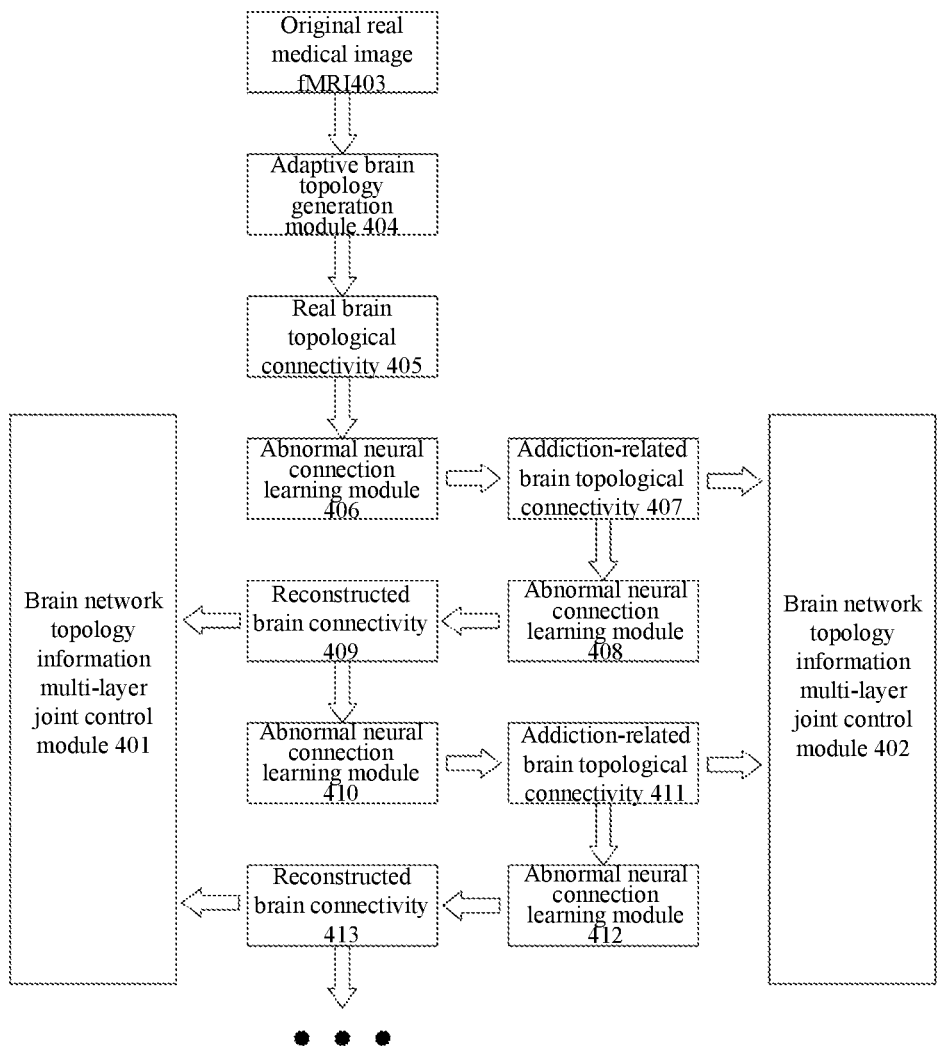
FIG. 4 is a schematic diagram of an addictive brain network topology information multi-level joint control model provided by an embodiment of the present application.

The addictive brain network analysis model shown in FIG. 3 is a fixed structure, and the overall structure of the entire model will not change during the training and testing of the model. In order to maintain the stability and rapid convergence of the model training process, a brain network topology information multi-layer joint control module is proposed. As shown in FIG. 4, FIG. 4 is a schematic diagram of an addictive brain network topology information multi-level joint control model provided by an embodiment of the present application. The addictive brain network topology information multi-level joint control model may include brain network topology information multi-level joint control module 401, brain network topology information multi-level joint control module 402, original real medical image fMRI 403, adaptive brain topology generation module 404, real brain topological connectivity 405, abnormal neural connection learning module 406, addiction-related brain topological connectivity 407, abnormal neural connection learning module 408, reconstructed brain connectivity 409, abnormal neural connection learning module 410, addiction-related brain topological connectivity 411, abnormal neural connection learning module 412, and reconstructed brain connectivity 413. In addition, the addictive brain network topology information multi-level joint control model can further include multiple abnormal neural connection learning modules to realize multi-layer reuse of abnormal neural connection learning modules, so that the expanded addictive brain network analysis model can fully learn more brain network topology information, thereby improving the overall performance of the model.

Figure 5:
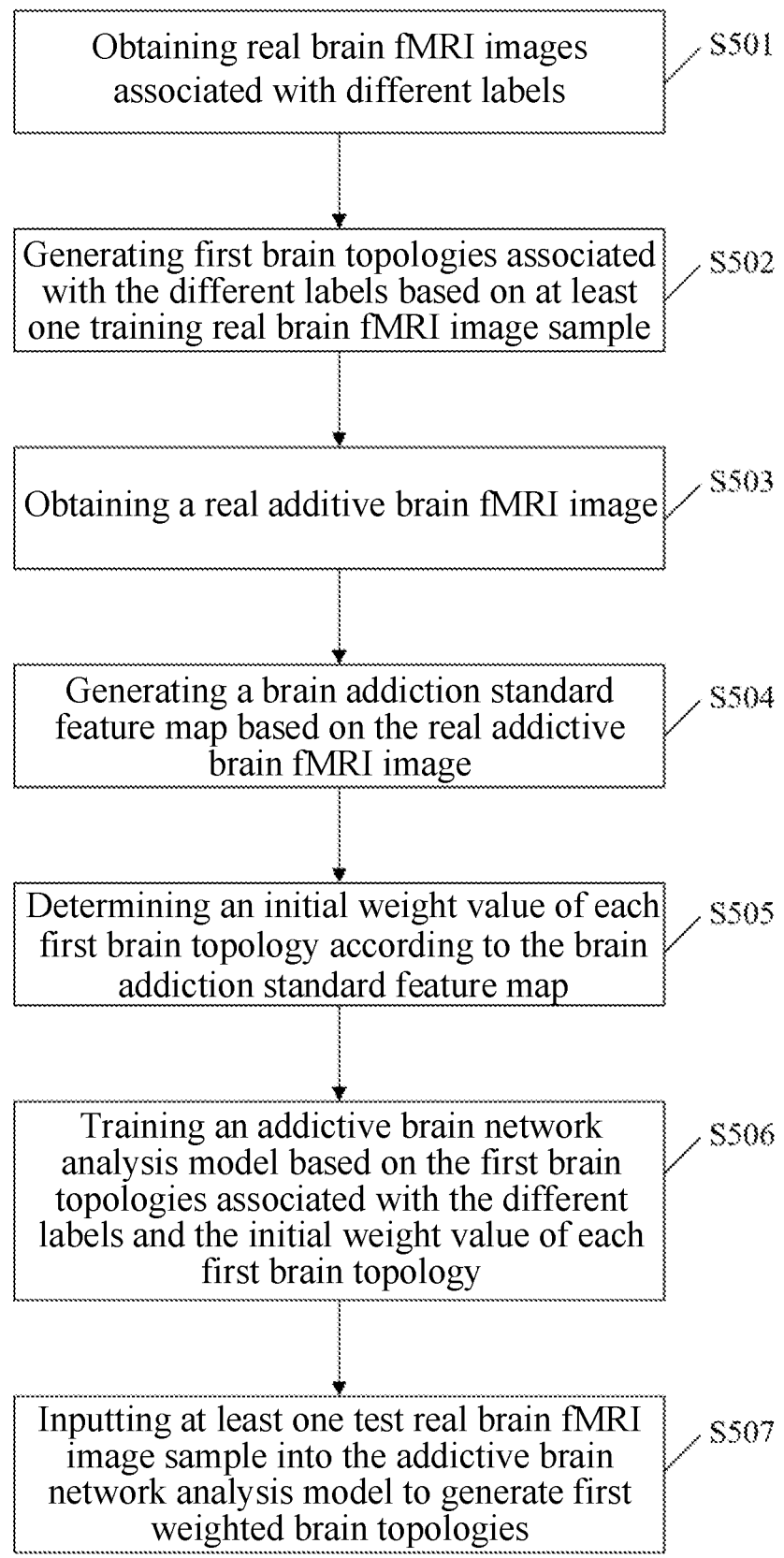
FIG. 5 is a flowchart of a brain network and brain addictive connectivity computing method provided by an embodiment of the present application.

Referring now to FIG. 5. FIG. 5 is a flowchart of a method for calculating a brain network and a brain addictive connectivity provided by an embodiment of the present application. The method includes but is not limited to the following operations:

S501: Obtaining real brain fMRI images associated with different labels.

The different labels above are used to indicate different concentrations of an addictive substance. The addictive substance may be nicotine. Inject rats with different concentrations of nicotine (for example, high-concentration nicotine, low-concentration nicotine, and saline) for two to three consecutive weeks to make rats addicted to different concentrations of nicotine, and collect real brain fMRI images of the rats, thus obtaining real brain fMRI images associated with different labels. When capturing real brain fMRI images of a rat, the whole capturing process is divided into two sections. The first section is to scan the brain of the rat at rest, the second section is to inject nicotine into the rat, and continue to scan the brain of the rat. For example, the capturing process of the real brain fMRI image is 40 minutes long, where the first 20 minutes is to scan the rat's brain at rest, then nicotine is injected at the 20-minute time point, after which the rat's brain continues to be scanned.

The above real brain fMRI images include multiple real brain regional fMRI images. The above real brain fMRI images associated with different labels may include training real brain fMRI image samples, validating real brain fMRI image samples and testing real brain fMRI image samples. The training real brain fMRI image samples are used to train an addictive brain network analysis model. The validating of the real brain fMRI image samples is used for validating the results of the addictive brain network analysis model and selecting the optimal model. The testing of the real brain fMRI image samples is used for evaluating the performance of addictive brain network analysis models. The training real brain fMRI image samples, the validating of the real brain fMRI image samples, and the testing of the real brain fMRI image samples may be divided according to a preset ratio.

S502: Based on the training real brain fMRI image samples, generating first brain topologies associated with the different labels.

The above-mentioned brain topological structure is the connectivity feature of the brain neural circuits.

Specifically, the collected training real brain fMRI images and brain atlas templates are input into the adaptive brain topology generation module, and the training real brain fMRI images are subjected to de-artifacting, time registration, and head movement correction, normalization, spatiotemporal filtering, etc. Then, the preprocessed brain fMRI image information is input to the resampling layer, and the brain fMRI images are resampled to the brain atlas template space, and then input to the time sequence extraction layer, and is divided into multiple brain regions according to ROI, and the average time sequence of pixels in each brain region is extracted. Finally, the first brain topologies associated with different labels are calculated according to the average time sequence.

S503: Obtaining addictive real brain fMRI images.

The above-mentioned addictive real brain fMRI images are real brain fMRI images related to nicotine addiction that have been published and obtained from professional doctors and professional institutions.

S504: Based on the addictive real brain fMRI images, generating a brain addiction standard feature map.

The above-mentioned brain addiction standard feature map is a brain topology map of brain nicotine addiction.

Specifically, the above-mentioned addictive real brain fMRI images are input into the prior knowledge guidance module, then through a deep neural network composed of convolutional layers, densely connected layers, and transition layers, a unified feature encoding extraction is performed on the input addictive real brain fMRI images. The brain addiction standard features extracted by the unified feature encoding are integrated with topological features to obtain the brain addiction standard feature map.

S505: Determining an initial weight value of each first brain topology according to the brain addiction standard feature map.

Specifically, the brain addiction standard feature map includes the connectivity information of multiple brain addiction abnormal regions and the weight distribution values of the various brain regions. Therefore, the weight distribution values of the various brain regions are determined as the initial weight values of the first brain topologies.

S506: Based on the first brain topologies associated with the different labels and the initial weight value of each first brain topologies, training an addictive brain network analysis model.

Specifically, the first brain topologies associated with the different labels include a first brain topology associated with a first label and a first brain topology associated with a second label, wherein the first label and the second label are used to indicate different concentrations of the addictive substance.

The first brain topology associated with the first label, the first brain topology associated with the second label, and the initial weight value of each first brain topology are input into the abnormal neural connection learning module composed of multiple deconvolutional layers. A class discrimination activation map Ax that distinguishes the first brain topology associated with the first label from the first brain topology associated with the second label is obtained through related convolution operations.

When the first label is the target label y, the class discrimination activation map Ax is added to the first brain topology x of the second label to obtain a fake sample x' of the first brain topology associated with the first label. Then, the fake sample x' of the first brain topology associated with the first label is input into the abnormal neural connection learning module through a random function, so as to obtain a second weighted brain topology $x_f$ of the first label. The fake sample x' of the first brain topology associated with the first label is expressed as:

$$x' = Ax + x;$$ (1-2)

The second weighted brain topology $x_f$ of the first label is expressed as:

$$x_f = Ax + x'; \quad (1\text{-}3)$$

When the second label is the target label y, add the class discrimination activation map Ax to the first brain topology x of the first label to obtain a fake sample x' of the first brain topology associated with the second label, and then input the fake sample x' of the first brain topology associated with the second label into the abnormal neural connection learning module through a random function to obtain a second weighted brain topology $x_f$ of the second label.

The first brain topology and the second weighted brain topology generated by the abnormal neural connection learning module that are of the same label are input into the brain atlas information feedback module composed of the convolutional layer, the transition layer and the fully connected layer, to perform topological feature extraction on the input first brain topology, and the obtained topological features are then integrated with the topological features extracted by the second weighted brain topology to determine the authenticity degree recognition result of the second weighted brain topology.

If the degree of authenticity of the second weighted brain topology is greater than or equal to a preset degree of authenticity, the loss function $L_a$ of the brain atlas information feedback module is obtained, and the loss function $L_a$ is back-propagated to iteratively train the brain atlas information feedback module, so that the brain atlas information feedback module determines that the authenticity of the second weighted brain topology is less than the preset authenticity, so as to obtain the trained brain atlas information feedback module.

If the degree of authenticity of the second weighted brain topology is less than the preset degree of authenticity, then obtain the loss function $L_G$ of the abnormal neural connection learning module. Through back-propagation of the loss function LG, the abnormal neural connection learning module is iteratively trained, so that the brain atlas information feedback module determines that the degree of authenticity of the second weighted brain topology is greater than or equal to the preset degree of authenticity, so as to obtain the trained abnormal neural connection learning module.

Further, the first brain topology and the second weighted brain topology generated by the abnormal neural connection learning module that are of the same label are input into the addiction pattern discrimination module composed of the convolutional layer, the transition layer and the fully connected layer, to perform the topological feature extraction on the input first brain topology. The extracted topological features are then integrated with the topological features extracted from the second weighted brain topology to determine the true or false recognition result of the second weighted brain topology.

If the recognition result of the second weighted brain topology is true, obtain the loss function $L_{cr}$ of the addiction pattern discrimination module. Through the back-propagation of the loss function $L_{cr}$, the addiction pattern discrimination module is iteratively trained, so that the addiction pattern discrimination module determines that the recognition result of the second weighted brain topology is false, and so the trained addiction pattern discrimination module is obtained. The loss function Lcr of the addiction pattern discrimination module is expressed as:

$$L_{cr} = E_{(x,y) \sim Preal(x,y)}[-\log P_c(y|x)] \quad (1\text{-}4)$$

where E( ) represents the expected value of the distribution function, x is the brain topology, y is the target label, and $(x,y) \sim P_{real}(x,y)$ represent the joint probability distribution of image annotation on brain topology x and target label y, $P_c(y|x)$ represents the conditional probability of being the target label y under the condition of the brain topology x.

If the recognition result of the second weighted brain topology is false, obtain the loss function Lcf of the abnormal neural connection learning module. Through the back-propagation of the loss function Lcf, the abnormal neural connection learning module is iteratively trained, so that the addiction pattern discrimination module determines that the recognition result of the second weighted brain topology is true, and so the trained abnormal neural connection learning module is obtained.

Finally, the addictive brain network analysis model is converged to Nash equilibrium, and the trained addictive brain network analysis model is obtained.

S507: inputting the testing real brain fMRI image samples into the addictive brain network analysis model to generate first weighted brain topologies.

The above-mentioned first weighted brain topologies are respective weighted brain topologies associated with the different labels.

Specifically, first, based on the testing real brain fMRI image samples, the second brain topologies associated with the different labels are generated. Next, the weight values in the second weighted brain topologies generated according to the trained addictive brain network analysis model are used as the initial weight values of the second brain topologies. Finally, first weighted brain topologies are generated based on the second brain topologies associated with the different labels and the initial weight values of the second brain topologies. The specific testing method is the same as the training method in S506, see S506 for more details, which will not be described here again.

Further, according to the generated first weighted brain topologies, abnormal brain topological features related to addiction are obtained, so as to accurately analyze the brain network of the addicted brain. For example, the differential brain connections between high-concentration nicotine samples and normal saline samples generated by the addiction brain network analysis module are highly consistent with the brain regions related to nicotine addiction (hippocampus, cortex, thalamus, ventral tegmental area, striatum, frontal lobe, etc.) obtained in professional doctors, professional institutions, and references.

In some embodiments, before inputting the testing real brain fMRI image samples into the addictive brain network analysis model and generating the first weighted brain topologies, it further includes:

inputting the validating real brain fMRI image samples into the addictive brain network analysis model, verifying the results of the addictive brain network analysis model, and selecting the optimal addictive brain network analysis model according to the results. The specific verifying method is the same as the training method in S506, see S506 for more details, which will not be described here again.

Methods according to the embodiments of the present application are described in detail above, and the devices of the embodiments of the present application are to be provided below.

Figure 6:
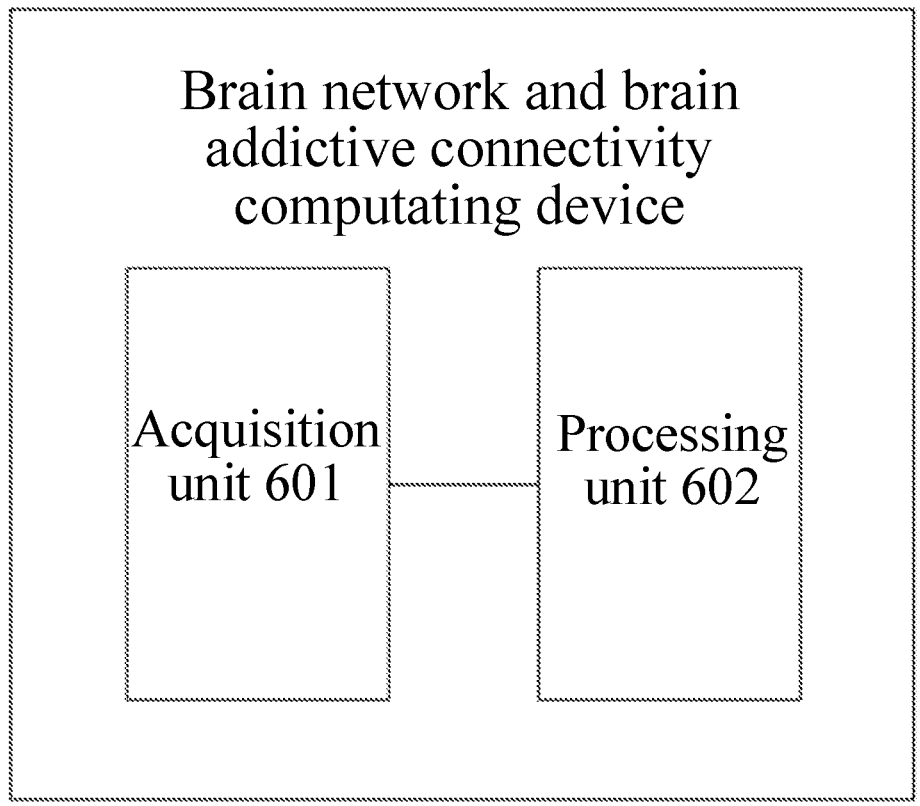
FIG. 6 is a schematic diagram of a brain network and brain addictive connectivity computing device 600 provided by an embodiment of the present application.

Referring to FIG. 6, FIG. 6 is a schematic diagram of a brain network and brain addictive connectivity computing device 600 provided by an embodiment of the present application. The device includes an acquisition unit 601 and a processing unit 602, and a detailed description of each unit is as follows.

The acquisition unit 601 is configured to capture real brain functional magnetic resonance fMRI images associated with different labels. The different labels are used to indicate different concentrations of an addictive substance. The real brain functional magnetic resonance fMRI images include a plurality of real brain regional fMRI images. The real brain fMRI images associated with different labels include training real brain fMRI image samples and testing real brain fMRI image samples.

The processing unit 602 is used to generate first brain topologies associated with the different labels based on the training real brain fMRI image samples.

The acquisition unit 601 is used to obtain an addictive real brain fMRI image.

The processing unit 602 is configured to generate a brain addiction standard feature map based on the addictive real brain fMRI image; determine an initial weight value of each first brain topology based on the brain addiction standard feature map; train an addictive brain network analysis model based on the first brain topologies associated with the different labels and the initial weight value of each first brain topology; and input the testing real brain fMRI image samples into the addictive brain network analysis model to generate first weighted brain topologies, where the first weighted brain topologies are respective weighted brain topologies associated with the different labels.

In a possible implementation, the acquisition unit 601 is further configured to: obtain a brain atlas template. The processing unit 602 is specifically configured to generate the first brain topologies associated with the different labels based on the training real brain fMRI image samples and the brain atlas template.

In a possible implementation, the processing unit 602 is specifically configured to: generate second brain topologies associated with the different labels based on the testing real brain fMRI image samples; determine an initial weight value of each second brain topology based on the addictive brain network analysis model; and generate first weighted brain topologies based on the second brain topologies associated with the different labels and an initial weight value of each second brain topology.

In a possible implementation, the processing unit 602 is specifically configured to: input the second brain topology associated with the first label and the second brain topology associated with the second label into the addictive brain network analysis model; when the first label is the target label, the first weighted brain topology associated with the first label is generated; and when the second label is the target label, the first weighted brain topology associated with the second label is generated.

In a possible implementation, the processing unit 602 is specifically configured to: input the first brain topologies associated with different labels and the initial weight value of each first brain topology into the addictive brain network analysis model to be trained to generate second weighted brain topologies; determine a recognition result of each second weighted brain topology; and train the addictive brain network analysis model according to the recognition result of each second weighted brain topology.

In a possible implementation, the acquisition unit 601 is further configured to: obtain a loss function of the addictive brain network analysis model based on the recognition result of each second weighted brain topology. The processing unit 602 is specifically configured to iteratively train the addictive brain network analysis model based on the loss function of the addictive brain network analysis model.

It should be noted that the implementation and beneficial effects of each unit may also correspond to the related description with reference to the method embodiment shown in FIG. 5.

Figure 7:
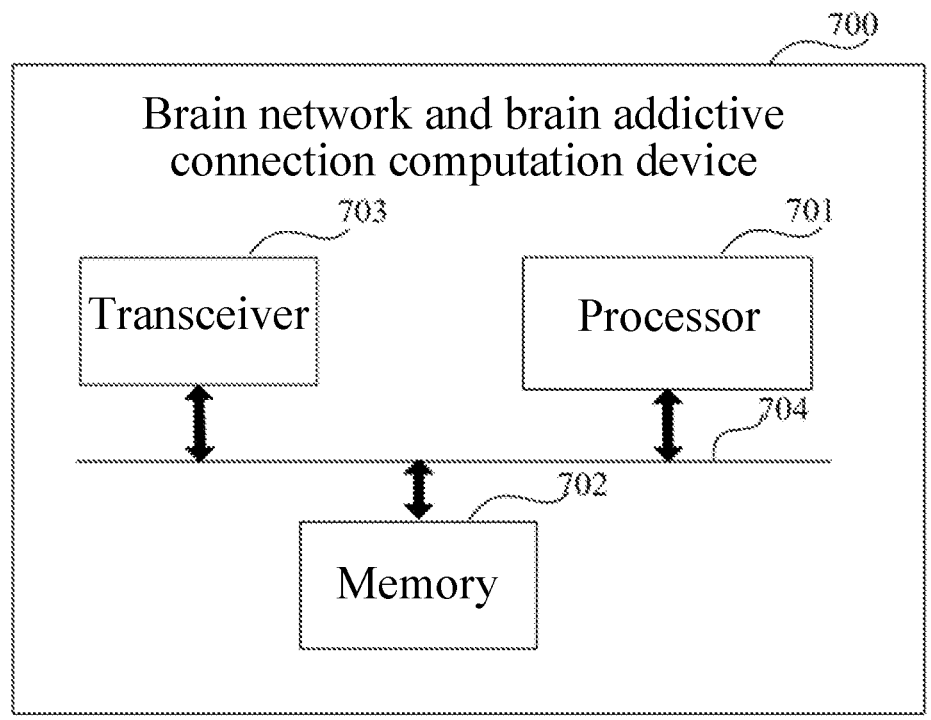
FIG. 7 is a schematic diagram of a brain network and brain addictive connectivity computing device 700 provided by an embodiment of the present application.

Referring to FIG. 7. FIG. 7 is a schematic diagram of a brain network and a brain addictive connectivity computing device 700 provided by an embodiment of the present application. The device 700 includes a processor 701, a transceiver 703, and optionally, a memory 702. The processor 701, the memory 702 and the transceiver 703 are connected to each other by a bus 704.

The memory 702 includes, but is not limited to, random access memory (RAM), read-only memory (ROM), erasable programmable read only memory (EPROM), or compact read-only memory (CD-ROM). The memory 702 is used for related instructions and data. The transceiver 703 is used to receive and transmit data.

The processor 701 may be one or more central processing units (CPUs). In the case where the processor 701 is a CPU, the CPU may be a single-core CPU or a multi-core CPU.

The processor 701 in the device 700 reads the program code stored in the memory 702 for performing the following operations: obtaining real brain functional magnetic resonance fMRI images associated with different labels through the transceiver 703; generating first brain topologies associated with the different labels based on the training real brain fMRI image samples; obtaining the addictive real brain fMRI images through the transceiver 703; generating a brain addiction standard feature map based on the addictive real brain fMRI images; determining the initial weight value of each first brain topology based on the brain addiction standard feature map; based on the first brain topologies associated with the different labels and the initial weight value of each first brain topology, training an addictive brain network analysis model; and inputting testing real brain fMRI image samples into the addictive brain network analysis model to generate first weighted brain topologies.

Optionally, the transceiver 703 is further configured to obtain a brain atlas template; the processor 701 is further configured to generate the first brain topologies associated with the different labels based on the training real brain fMRI image samples and the brain atlas template.

Optionally, the processor 701 is further used for: based on the testing real brain fMRI image samples, generating second brain topologies associated with the different labels; determining an initial weight value of each second brain topology according to the addictive brain network analysis model; generating first weighted brain topologies based on the second brain topologies associated with the different labels and the initial weight value of each second brain topology.

Optionally, the processor 701 is further configured to: input the second brain topology associated with the first label and the second brain topology associated with the second label into the addictive brain network analysis model; when the first label is a target label, generate a first weighted brain topology associated with the first label; and when the second label is the target label, generate a first weighted brain topology associated with the second label.

Optionally, the processor 701 is further configured to: input the first brain topology associated with the different labels and the initial weight value of each first brain topology into the addictive brain network analysis model to be trained to generate second weighted brain topologies; determine a recognition result of each second weighted brain topology; train the addictive brain network analysis model based on the recognition result of each second weighted brain topology.

Optionally, the transceiver 703 is further configured to obtain the loss function of the addictive brain network analysis model according to the recognition result of each second weighted brain topology. The processor 701 is further configured to iteratively train the addictive brain network analysis model according to the loss function of the addictive brain network analysis model.

It should be noted that, the implementation and beneficial effects of each operation may also correspond to the related description with reference to the method embodiment shown in FIG. 5.

An embodiment of the present application further provides a chip system, which includes a processor, which is configured to support a server to implement the functions involved in any of the foregoing embodiments. In a possible design, the chip system may further include a memory for locating computer programs and data necessary for the server. The chip system may consist of chips, or may include chips and other discrete devices. The input and output of the chip system respectively correspond to the receiving and sending operations of the server in the method embodiments.

Embodiments of the present application further provide a brain network and brain addictive connectivity computing device, including a processor and an interface. The processor may be used to perform the methods in the above method embodiments.

It should be understood that the above-mentioned device for analyzing the addictive brain network may be a chip. For example, the addictive brain network analysis device may be a field programmable gate array (FPGA), an application specific integrated circuit (ASIC), or a system on chip (SoC), a central processing unit (CPU), a network processor (NP), a digital signal processing circuit (DSP), or a micro controller unit (MCU), or may also be a programmable logic device (PLD) or other integrated chips.

In the implementation process, each step of the above-mentioned methods may be completed by a hardware integrated logic circuit in a processor or an instruction in the form of software. The steps of the method disclosed in connection with the embodiments of the present application may be directly embodied as being executed by a hardware processor, or executed by a combination of hardware and software modules in the processor. The software module may be located in random access memory, flash memory, read-only memory, programmable read-only memory or electrically erasable programmable memory, registers and other storage media that are mature in the art. The storage medium is located in the memory, and the processor reads the information in the memory and performs the steps of the above method in combination with its hardware. To avoid repetition, detailed description is omitted here.

It should be noted that the processor in this embodiment of the present application may be an integrated circuit chip, which has a signal processing capability. In the implementation process, each step of the above method embodiments may be executed by a hardware integrated logic circuit in a processor or an instruction in the form of software. The aforementioned processors may be general purpose processors, digital signal processors (DSPs), application specific integrated circuits (ASICs), field programmable gate arrays (FPGAs) or other programmable logic devices, discrete gate or transistor logic devices, or discrete hardware components. They can implement or execute the methods, steps and logic block diagrams disclosed in the embodiments of this application. A general purpose processor may be a microprocessor or any conventional processor or the like. The steps of the methods disclosed in combination with the embodiments of the present application may be directly embodied as being executed and completed by a hardware decoding processor, or executed and completed by a combination of hardware and software modules in the decoding processor. The software modules may be located in random access memory, flash memory, read-only memory, programmable read-only memory or electrically erasable programmable memory, registers and other storage media mature in the art. The storage medium is located in the memory, and the processor reads the information in the memory and completes the steps of the above method in combination with its hardware.

According to the method provided by the embodiment of the present application, the present application further provides a computer program product. The computer program product includes a computer program that, when running on a computer, causes the computer to perform the method of any one of the embodiments shown in FIG. 5.

According to the method provided by the embodiment of the present application, the present application further provides a computer-readable medium, where a computer program is stored in the computer-readable medium, and when the computer program runs on a computer, the computer is made to execute the method of any one of the embodiments shown in FIG. 5.

According to the method provided by the embodiments of the present application, the present application further provides an addictive brain network analysis system, which includes the aforementioned one or more servers and one or more terminal devices.

In the above-mentioned embodiments, it may be implemented in whole or in part by software, hardware, firmware or any combination thereof. When implemented in software, it may be implemented in whole or in part in the form of a computer program product. The computer program product includes one or more computer instructions. When the computer instructions are loaded and executed on a computer, all or part of the processes or functions described in the embodiments of the present application are created. The computer may be a general purpose computer, a special purpose computer, a computer network, or other programmable devices. The computer instructions may be stored in a computer-readable storage medium, or transmitted from one computer-readable storage medium to another computer-readable storage medium. For example, the computer instructions may be transmitted in a wired manner (e.g., coaxial cable, fiber optic, digital subscriber line (DSL)) or in a wireless manner (e.g., infrared, wireless, microwave, etc.) from a website site, computer, server, or data center to another website site, computer, server or data center. The computer-readable storage medium may be any available medium or a data storage device such as a server, data center, or the like that is an integration of one or more available media that may be accessed by a computer. The available media may be magnetic media (e.g., floppy disks, hard disks, magnetic tapes), optical media (e.g., high-density digital video discs (DVDs)), or semiconductor media (e.g., solid state discs, SSD)), etc.

Those of ordinary skill in the art will appreciate that the various illustrative logical blocks and steps described in connection with the embodiments disclosed herein may be implemented in in the form electronic hardware, or in the form of a combination of computer software and electronic hardware. Whether these functions are performed in hardware or software depends on the specific application and design constraints of the technical solution. Skilled artisans may implement the described functionality using different methods for each particular application, but such implementations should not be considered beyond the scope of this application.

Those skilled in the art can clearly understand that, for the convenience and brevity of description, the specific working process of the above-described systems, devices and units may refer to the corresponding processes in the foregoing method embodiments, and so are not to be repeated here.

The functions, if implemented in the form of software functional units and sold or used as stand-alone products, may be stored in a computer-readable storage medium. Based on this understanding, the essence of technical solution of the present application, or in other words the part that contributes to the prior art, or part of the technical solution may be embodied in the form of a software product. The computer software product is stored in a storage medium, and includes multiple instructions for causing a computer device (which may be a personal computer, a server, or a positioning server, etc.) to execute all or part of the steps of the methods described in the various embodiments of the present application. The aforementioned storage medium includes: U disk, removable hard disk, read-only memory (ROM), random access memory (RAM), magnetic disk or optical disk and other media that can store program codes.

The foregoing merely illustrates some specific embodiments of the present application, but the scope of protection of the present application will not be limited thereto. Any person skilled in the art can easily think of changes or substitutions within the technical scope disclosed in this application, which shall all be covered within the protection scope of this application. Therefore, the protection scope of the present application should be subject to the protection scope of the appended claims. Embodiments of the present application will be described below with reference to the accompanying drawings in the embodiments of the present application.

What is claimed is:

1. A brain network and brain addictive connectivity computing method, comprising:
    obtaining a plurality of real brain functional magnetic resonance (fMRI) images associated with different labels; wherein the different labels are used to indicate different concentrations of an addictive substance; the plurality of real brain fMRI images comprise a plurality of real brain regional fMRI images, and the plurality of real brain fMRI images associated with the different labels comprise at least one training real brain fMRI image sample and at least one testing real brain fMRI image sample;
    generating first brain topologies associated with the different labels based on the at least one training real brain fMRI image sample and a brain atlas template, each first brain topology being a connectivity feature of a brain neural circuit;
    obtaining an addictive real brain fMRI image, which is a published real brain fMRI image that is associated with brain nicotine addiction and that is obtained from a professional doctor or professional institution;
    generating a brain addiction standard feature map based on the addictive real brain fMRI image, wherein the brain addiction standard feature map comprises connectivity information of a plurality of brain addictive abnormal regions and a weight distribution value of each brain addictive abnormal region;
    determining an initial weight value of each of the first brain topologies according to the brain addiction standard feature map;
    training an addictive brain network analysis model based on the first brain topologies associated with the different labels and the initial weight value of each of the first brain topologies; and
    inputting the at least one testing real brain fMRI image sample into the addictive brain network analysis model to generate first weighted brain topologies, the first weighted brain topologies being respective weighted brain topologies associated with the different labels.

2. The brain network and brain addictive connectivity computing method of claim 1, wherein inputting the at least one testing real brain fMRI image sample into the addictive brain network analysis model to generate the first weighted brain topologies comprises:
    generating second brain topologies associated with the different labels based on the at least one testing real brain fMRI image sample; determining an initial weight value of each of the second brain topologies based on the addictive brain network analysis model; and
    generating the first weighted brain topologies based on the second brain topologies associated with the different labels and the initial weight value of each of the second brain topologies.

3. The brain network and brain addictive connectivity computing method of claim 2, wherein the second brain topologies associated with the different labels comprise a second brain topology associated with a first label and a second brain topology associated with a second label; the first weighted brain topologies comprise a first weighted brain topology associated with the first label and a first weighted brain topology associated with the second label;
    wherein generating the first weighted brain topologies based on the second brain topologies associated with the different labels and the initial weight value of each of the second brain topologies comprises:
    inputting the second brain topology associated with the first label and the second brain topology associated with the second label into the addictive brain network analysis model;
    in response to the first label being a target label, generating the first weighted brain topology associated with the first label; and in response to the second label being the target label, generating the first weighted brain topology associated with the second label.

4. The brain network and brain addictive connectivity computing method of claim 1, wherein training the addictive brain network analysis model based on the first brain topologies associated with the different labels and the initial weight value of each of the first brain topologies comprises:
    inputting the first brain topologies associated with the different labels and the initial weight value of each of the first brain topologies into the addictive brain network analysis model to be trained to generate second weighted brain topologies;
    determining a recognition result of each of the second weighted brain topologies; and
    training the addictive brain network analysis model based on the recognition result of each second weighted brain topology.

5. The brain network and brain addictive connectivity computing method of claim 4, wherein training the addictive brain network analysis model according to the recognition result of each second weighted brain topology comprises:

obtaining a loss function of the addictive brain network analysis model according to the recognition result of each of the second weighted brain topologies; and iteratively training the addictive brain network analysis model according to the loss function of the addictive brain network analysis model.

6. A brain network and brain addictive connectivity computing device, comprising a processor and a memory, wherein the memory is configured to store a computer program, and the processor is configured to call the computer program to perform a brain network and brain addictive connectivity computing method comprising:

obtaining a plurality of real brain functional magnetic resonance (fMRI) images associated with different labels; wherein the different labels are used to indicate different concentrations of an addictive substance; the plurality of real brain fMRI images comprise a plurality of real brain regional fMRI images, and the plurality of real brain fMRI images associated with the different labels comprise at least one training real brain fMRI image sample and at least one testing real brain fMRI image sample;

generating first brain topologies associated with the different labels based on the at least one training real brain fMRI image sample and a brain atlas template, each first brain topology being a connectivity feature of a brain neural circuit;

obtaining an addictive real brain fMRI image, which is a published real brain fMRI image that is associated with brain nicotine addiction and that is obtained from a professional doctor or professional institution;

generating a brain addiction standard feature map based on the addictive real brain fMRI image, wherein the brain addiction standard feature map comprises connectivity information of a plurality of brain addictive abnormal regions and a weight distribution value of each brain addictive abnormal region;

determining an initial weight value of each of the first brain topologies according to the brain addiction standard feature map;

training an addictive brain network analysis model based on the first brain topologies associated with the different labels and the initial weight value of each of the first brain topologies; and inputting the at least one testing real brain fMRI image sample into the addictive brain network analysis model to generate first weighted brain topologies, the first weighted brain topologies being respective weighted brain topologies associated with the different labels.

7. The brain network and brain addictive connectivity computing device of claim 6, wherein inputting the at least one testing real brain fMRI image sample into the addictive brain network analysis model to generate the first weighted brain topologies comprises:

generating second brain topologies associated with the different labels based on the at least one testing real brain fMRI image sample; determining an initial weight value of each of the second brain topologies based on the addictive brain network analysis model; and generating the first weighted brain topologies based on the second brain topologies associated with the different labels and the initial weight value of each of the second brain topologies.

8. The brain network and brain addictive connectivity computing device of claim 7, wherein the second brain topologies associated with the different labels comprise a second brain topology associated with a first label and a second brain topology associated with a second label; the first weighted brain topologies comprise a first weighted brain topology associated with the first label and a first weighted brain topology associated with the second label;

wherein generating the first weighted brain topologies based on the second brain topologies associated with the different labels and the initial weight value of each of the second brain topologies comprises:

inputting the second brain topology associated with the first label and the second brain topology associated with the second label into the addictive brain network analysis model;

in response to the first label being a target label, generating the first weighted brain topology associated with the first label; and in response to the second label being the target label, generating the first weighted brain topology associated with the second label.

9. The brain network and brain addictive connectivity computing device of claim 6, wherein training the addictive brain network analysis model based on the first brain topologies associated with the different labels and the initial weight value of each of the first brain topologies comprises:

inputting the first brain topologies associated with the different labels and the initial weight value of each of the first brain topologies into the addictive brain network analysis model to be trained to generate second weighted brain topologies;

determining a recognition result of each of the second weighted brain topologies; and training the addictive brain network analysis model based on the recognition result of each second weighted brain topology.

10. The brain network and brain addictive connectivity computing device of claim 9, wherein training the addictive brain network analysis model according to the recognition result of each second weighted brain topology comprises:

obtaining a loss function of the addictive brain network analysis model according to the recognition result of each of the second weighted brain topologies; and iteratively training the addictive brain network analysis model according to the loss function of the addictive brain network analysis model.

11. A chip, being a chip in an addictive brain network analysis device; wherein the chip comprises a processor, and an input interface and an output interface coupled to the processor; the chip further comprises a memory, when the computer program in the memory is executed the method of claim 1 is performed.

12. A non-transitory computer-readable storage medium, configured for storing a computer program, wherein when the computer program is run on a computer, the computer is caused to perform a brain network and brain addictive connectivity computing method, the brain network and brain addictive connectivity computing method comprising:

obtaining a plurality of real brain functional magnetic resonance (fMRI) images associated with different labels; wherein the different labels are used to indicate different concentrations of an addictive substance; the plurality of real brain fMRI images comprise a plurality of real brain regional fMRI images, and the plurality of real brain fMRI images associated with the different labels comprise at least one training real brain fMRI image sample and at least one testing real brain fMRI image sample;

generating first brain topologies associated with the different labels based on the at least one training real brain fMRI image sample and a brain atlas template, each first brain topology being a connectivity feature of a brain neural circuit;

obtaining an addictive real brain fMRI image, which is a published real brain fMRI image that is associated with brain nicotine addiction and that is obtained from a professional doctor or professional institution;

generating a brain addiction standard feature map based on the addictive real brain fMRI image, wherein the brain addiction standard feature map comprises connectivity information of a plurality of brain addictive abnormal regions and a weight distribution value of each brain addictive abnormal region;

determining an initial weight value of each of the first brain topologies according to the brain addiction standard feature map;

training an addictive brain network analysis model based on the first brain topologies associated with the different labels and the initial weight value of each of the first brain topologies; and inputting the at least one testing real brain fMRI image sample into the addictive brain network analysis model to generate first weighted brain topologies, the first weighted brain topologies being respective weighted brain topologies associated with the different labels.

13. The non-transitory computer-readable storage medium of claim 12, wherein inputting the at least one testing real brain fMRI image sample into the addictive brain network analysis model to generate the first weighted brain topologies comprises:

generating second brain topologies associated with the different labels based on the at least one testing real brain fMRI image sample; determining an initial weight value of each of the second brain topologies based on the addictive brain network analysis model; and generating the first weighted brain topologies based on the second brain topologies associated with the different labels and the initial weight value of each of the second brain topologies.

14. The non-transitory computer-readable storage medium of claim 13, wherein the second brain topologies associated with the different labels comprise a second brain topology associated with a first label and a second brain topology associated with a second label; the first weighted brain topologies comprise a first weighted brain topology associated with the first label and a first weighted brain topology associated with the second label;

wherein generating the first weighted brain topologies based on the second brain topologies associated with the different labels and the initial weight value of each of the second brain topologies comprises:

inputting the second brain topology associated with the first label and the second brain topology associated with the second label into the addictive brain network analysis model;

in response to the first label being a target label, generating the first weighted brain topology associated with the first label; and in response to the second label being the target label, generating the first weighted brain topology associated with the second label.

15. The non-transitory computer-readable storage medium of claim 12, wherein training the addictive brain network analysis model based on the first brain topologies associated with the different labels and the initial weight value of each of the first brain topologies comprises:

inputting the first brain topologies associated with the different labels and the initial weight value of each of the first brain topologies into the addictive brain network analysis model to be trained to generate second weighted brain topologies;

determining a recognition result of each of the second weighted brain topologies; and training the addictive brain network analysis model based on the recognition result of each second weighted brain topology.

16. The non-transitory computer-readable storage medium of claim 15, wherein training the addictive brain network analysis model according to the recognition result of each second weighted brain topology comprises:

obtaining a loss function of the addictive brain network analysis model according to the recognition result of each of the second weighted brain topologies; and iteratively training the addictive brain network analysis model according to the loss function of the addictive brain network analysis model.

* * * * *